(12) United States Patent
Bedard et al.

(10) Patent No.: US 10,160,697 B2
(45) Date of Patent: Dec. 25, 2018

(54) METHANE CONVERSION APPARATUS AND PROCESS USING A SUPERSONIC FLOW REACTOR

(71) Applicant: UOP LLC, Des Plaines, IL (US)

(72) Inventors: Robert L. Bedard, McHenry, IL (US); Christopher Naunheimer, Arlington Heights, IL (US); Gavin P. Towler, Inverness, IL (US); Laura E. Leonard, Western Springs, IL (US); Gregory O. Woodcock, Mesa, AZ (US); Donald L. Mittendorf, Mesa, AZ (US); Aziz Sattar, West Chicago, IL (US); Christopher D. Gatto, Gilbert, AZ (US); Robert S. Murray, Garden Valley, ID (US)

(73) Assignee: UOP LLC, Des Plaines, IL (US)

( * ) Notice: Subject to any disclaimer, the term of this patent is extended or adjusted under 35 U.S.C. 154(b) by 37 days.

(21) Appl. No.: 15/630,146

(22) Filed: Jun. 22, 2017

(65) Prior Publication Data
US 2017/0291861 A1 Oct. 12, 2017

Related U.S. Application Data

(63) Continuation-in-part of application No. 13/967,391, filed on Aug. 15, 2013, now Pat. No. 9,707,530.

(60) Provisional application No. 61/691,321, filed on Aug. 21, 2012.

(51) Int. Cl.
*B01J 19/02* (2006.01)
*B01J 19/26* (2006.01)
*C07C 2/78* (2006.01)
*C10G 50/00* (2006.01)
(Continued)

(52) U.S. Cl.
CPC ............ *C07C 2/78* (2013.01); *B01J 6/008* (2013.01); *B01J 19/02* (2013.01); *B01J 19/2415* (2013.01); *B01J 19/26* (2013.01); *C10G 50/00* (2013.01); *B01J 2219/00094* (2013.01); *B01J 2219/00123* (2013.01); *B01J 2219/00157* (2013.01); *B01J 2219/0204* (2013.01); *B01J 2219/029* (2013.01); *B01J 2219/0236* (2013.01); *B01J 2219/0263* (2013.01); *B01J 2219/0281* (2013.01); *B01J 2219/0286* (2013.01); *C10G 2300/1025* (2013.01); *C10G 2400/24* (2013.01)

(58) Field of Classification Search
CPC ..................................................... C10H 19/00
See application file for complete search history.

(56) References Cited

U.S. PATENT DOCUMENTS 2,985,698 A * 5/1961 Nikolaus Pechtold ... C07C 4/04
585/324
3,408,417 A * 10/1968 Sogawa ..................... C07C 4/04
585/541
(Continued)

FOREIGN PATENT DOCUMENTS

GB 1199483 A 7/1970
JP 2007262514 A 10/2007

*Primary Examiner* — Matthew J Merkling

(57) ABSTRACT

Apparatus and methods are provided for converting methane in a feed stream to acetylene. A hydrocarbon stream is introduced into a supersonic reactor and pyrolyzed to convert at least a portion of the methane to acetylene. The reactor effluent stream may be treated to convert acetylene to another hydrocarbon process.

19 Claims, 7 Drawing Sheets

(51) Int. Cl.
    *B01J 19/24*     (2006.01)
    *B01J 6/00*     (2006.01)

(56) References Cited

U.S. PATENT DOCUMENTS

| | | | | |
|---|---|---|---|---|
| 3,414,247 | A * | 12/1968 | Sama Saverio A | F28O 3/06 |
| | | | | 261/118 |
| 3,563,709 | A * | 2/1971 | Staud et al. | C10G 9/36 |
| | | | | 422/208 |
| 3,865,581 | A * | 2/1975 | Sekino | C22C 19/058 |
| | | | | 420/36 |
| 4,136,015 | A * | 1/1979 | Kamm | B01J 19/26 |
| | | | | 208/129 |
| 4,278,446 | A * | 7/1981 | Von Rosenberg, Jr. | |
| | | | | C10J 3/485 |
| | | | | 252/373 |
| 4,582,678 | A * | 4/1986 | Niino | B22F 7/06 |
| | | | | 29/423 |
| 4,708,828 | A * | 11/1987 | Plannerer | F02M 3/12 |
| | | | | 261/121.3 |
| 4,724,272 | A * | 2/1988 | Raniere | C10G 9/38 |
| | | | | 208/129 |
| 4,762,168 | A * | 8/1988 | Kawabe | F28B 11/00 |
| | | | | 165/11.1 |
| 4,841,723 | A | 6/1989 | Lau et al. | |
| 5,219,530 | A * | 6/1993 | Hertzberg | G10K 15/043 |
| | | | | 208/128 |
| 5,248,408 | A * | 9/1993 | Owen | B01J 8/0055 |
| | | | | 208/113 |
| 5,259,856 | A * | 11/1993 | Ohga | C03B 37/01446 |
| | | | | 65/423 |
| 5,324,904 | A * | 6/1994 | Cresswell | B01J 19/0013 |
| | | | | 219/618 |
| 5,531,066 | A * | 7/1996 | Pfefferle | F02C 7/264 |
| | | | | 431/268 |
| 5,565,393 | A * | 10/1996 | Felix | B01J 19/02 |
| | | | | 422/241 |
| 5,615,627 | A * | 4/1997 | Marr, Jr. | C10B 3/00 |
| | | | | 110/236 |
| 5,720,163 | A * | 2/1998 | Pfefferle | F01N 3/18 |
| | | | | 431/7 |
| 5,873,950 | A * | 2/1999 | Ganesan | C22C 19/053 |
| | | | | 148/206 |
| 6,134,785 | A * | 10/2000 | Walter | B23P 15/008 |
| | | | | 29/890.054 |
| 6,217,286 | B1 * | 4/2001 | Huang | B22D 27/045 |
| | | | | 148/404 |
| 6,699,604 | B1 * | 3/2004 | Li | C04B 41/009 |
| | | | | 156/89.27 |
| 7,150,931 | B1 * | 12/2006 | Jaffrey | H01M 8/0204 |
| | | | | 429/465 |
| 8,636,958 | B2 * | 1/2014 | Salazar-Guillen | B01J 19/26 |
| | | | | 422/129 |
| 9,328,038 | B2 | 5/2016 | Shafe et al. | |
| 2001/0001897 | A1 * | 5/2001 | Zhao | B23P 15/04 |
| | | | | 29/889 |
| 2001/0014436 | A1 * | 8/2001 | Lemelson | F23N 1/022 |
| | | | | 1/22 |
| 2002/0025272 | A1 * | 2/2002 | Witherspoon | B22F 3/087 |
| | | | | 419/66 |
| 2002/0056548 | A1 * | 5/2002 | Nakamura | B24B 57/02 |
| | | | | 165/154 |
| 2002/0128161 | A1 * | 9/2002 | Wickham | C10G 9/16 |
| | | | | 508/541 |
| 2002/0192494 | A1 * | 12/2002 | Tzatzov | C23C 26/00 |
| | | | | 428/655 |
| 2003/0010035 | A1 * | 1/2003 | Farmer | C23C 4/00 |
| | | | | 60/752 |
| 2003/0236312 | A1 * | 12/2003 | O'Rear | C01B 3/02 |
| | | | | 518/728 |
| 2004/0011439 | A1 * | 1/2004 | Corrigan | C22C 19/056 |
| | | | | 148/555 |
| 2004/0018144 | A1 * | 1/2004 | Briscoe | C01B 3/323 |
| | | | | 423/652 |
| 2005/0058851 | A1 * | 3/2005 | Smith | B21C 23/22 |
| | | | | 428/685 |
| 2005/0120981 | A1 * | 6/2005 | Ferguson | F24H 1/40 |
| | | | | 122/367.3 |
| 2006/0038044 | A1 * | 2/2006 | Van Steenkiste | B05B 7/1486 |
| | | | | 239/594 |
| 2006/0104878 | A1 * | 5/2006 | Chiu | F23G 5/50 |
| | | | | 423/240 R |
| 2006/0216429 | A1 * | 9/2006 | Bengtsson | C23C 4/06 |
| | | | | 427/446 |
| 2007/0144622 | A1 * | 6/2007 | Flahaut | C22C 19/053 |
| | | | | 148/419 |
| 2007/0163749 | A1 * | 7/2007 | Miyahara | H01L 23/473 |
| | | | | 165/80.3 |
| 2007/0217995 | A1 * | 9/2007 | Matsumura | C25B 1/04 |
| | | | | 423/657 |
| 2007/0235110 | A1 * | 10/2007 | Yoshinari | C22C 19/057 |
| | | | | 148/428 |
| 2007/0260101 | A1 * | 11/2007 | Carrera | B01D 53/228 |
| | | | | 585/654 |
| 2008/0033221 | A1 * | 2/2008 | Hori | B01J 23/44 |
| | | | | 585/273 |
| 2008/0093583 | A1 * | 4/2008 | van den Oosterkamp | |
| | | | | B01J 8/025 |
| | | | | 252/373 |
| 2009/0000184 | A1 * | 1/2009 | Garwood | B01F 7/00875 |
| | | | | 44/307 |
| 2009/0211255 | A1 * | 8/2009 | Simons | F23R 3/18 |
| | | | | 60/737 |
| 2009/0283451 | A1 * | 11/2009 | Srinivas | C07C 4/04 |
| | | | | 208/48 AA |
| 2010/0020848 | A1 * | 1/2010 | Nazmy | C22C 19/057 |
| | | | | 374/179 |
| 2010/0199559 | A1 * | 8/2010 | Hallett | B01J 4/005 |
| | | | | 48/127.7 |
| 2010/0216079 | A1 * | 8/2010 | Targoff | F23D 11/441 |
| | | | | 431/8 |
| 2010/0290978 | A1 * | 11/2010 | Chun | B01J 4/002 |
| | | | | 423/445 R |
| 2010/0314788 | A1 * | 12/2010 | Hung | B01J 2/003 |
| | | | | 264/5 |
| 2011/0083435 | A1 * | 4/2011 | Palmer | F23D 1/00 |
| | | | | 60/650 |
| 2011/0289842 | A1 * | 12/2011 | Oldenburg | C10J 3/485 |
| | | | | 48/61 |
| 2011/0300357 | A1 * | 12/2011 | Witz | C23C 4/02 |
| | | | | 428/213 |
| 2012/0023823 | A1 * | 2/2012 | D'Agostini | F23G 5/12 |
| | | | | 48/197 R |
| 2012/0117976 | A1 * | 5/2012 | Krull | F02C 7/264 |
| | | | | 60/776 |
| 2013/0041050 | A1 * | 2/2013 | Luzenski | B01J 19/0093 |
| | | | | 518/706 |
| 2014/0058149 | A1 | 2/2014 | Negiz et al. | |
| 2014/0058176 | A1 | 2/2014 | Bedard et al. | |
| 2014/0116669 | A1 * | 5/2014 | Li | F28F 3/02 |
| | | | | 165/185 |

* cited by examiner

METHANE CONVERSION APPARATUS AND PROCESS USING A SUPERSONIC FLOW REACTOR

CROSS-REFERENCE TO RELATED APPLICATION

This application is a Continuation-In-Part of copending application Ser. No. 13/967,391 filed Aug. 15, 2013, which application claims priority from Provisional Application No. 61/691,321 filed Aug. 21, 2012, now expired, the contents of which cited applications are hereby incorporated by reference in their entirety.

FIELD

Apparatus and methods are disclosed for converting methane in a hydrocarbon stream to acetylene using a supersonic flow reactor.

BACKGROUND

Light olefin materials, including ethylene and propylene, represent a large portion of the worldwide demand in the petrochemical industry. Light olefins are used in the production of numerous chemical products via polymerization, oligomerization, alkylation and other well-known chemical reactions. These light olefins are essential building blocks for the modern petrochemical and chemical industries. Producing large quantities of light olefin material in an economical manner, therefore, is a focus in the petrochemical industry. The main source for these materials in present day refining is the steam cracking of petroleum feeds.

The cracking of hydrocarbons brought about by heating a feedstock material in a furnace has long been used to produce useful products, including for example, olefin products. For example, ethylene, which is among the more important products in the chemical industry, can be produced by the pyrolysis of feedstocks ranging from light paraffins, such as ethane and propane, to heavier fractions such as naphtha. Typically, the lighter feedstocks produce higher ethylene yields (50-55% for ethane compared to 25-30% for naphtha); however, the cost of the feedstock is more likely to determine which is used. Historically, naphtha cracking has provided the largest source of ethylene, followed by ethane and propane pyrolysis, cracking, or dehydrogenation. Due to the large demand for ethylene and other light olefinic materials, however, the cost of these traditional feeds has steadily increased.

Energy consumption is another cost factor impacting the pyrolytic production of chemical products from various feedstocks. Over the past several decades, there have been significant improvements in the efficiency of the pyrolysis process that have reduced the costs of production. In a typical or conventional pyrolysis plant, a feedstock passes through a plurality of heat exchanger tubes where it is heated externally to a pyrolysis temperature by the combustion products of fuel oil or natural gas and air. One of the more important steps taken to minimize production costs has been the reduction of the residence time for a feedstock in the heat exchanger tubes of a pyrolysis furnace. Reduction of the residence time increases the yield of the desired product while reducing the production of heavier by-products that tend to foul the pyrolysis tube walls. However, there is little room left to improve the residence times or overall energy consumption in traditional pyrolysis processes.

More recent attempts to decrease light olefin production costs include utilizing alternative processes and/or feed streams. In one approach, hydrocarbon oxygenates and more specifically methanol or dimethylether (DME) are used as an alternative feedstock for producing light olefin products. Oxygenates can be produced from available materials such as coal, natural gas, recycled plastics, various carbon waste streams from industry and various products and by-products from the agricultural industry. Making methanol and other oxygenates from these types of raw materials is well established and typically includes one or more generally known processes such as the manufacture of synthesis gas using a nickel or cobalt catalyst in a steam reforming step followed by a methanol synthesis step at relatively high pressure using a copper-based catalyst.

Once the oxygenates are formed, the process includes catalytically converting the oxygenates, such as methanol, into the desired light olefin products in an oxygenate to olefin (OTO) process. Techniques for converting oxygenates, such as methanol to light olefins (MTO), are described in U.S. Pat. No. 4,387,263, which discloses a process that utilizes a catalytic conversion zone containing a zeolitic type catalyst. U.S. Pat. No. 4,587,373 discloses using a zeolitic catalyst like ZSM-5 for purposes of making light olefins. U.S. Pat. No. 5,095,163; U.S. Pat. No. 5,126,308 and U.S. Pat. No. 5,191,141 on the other hand, disclose an MTO conversion technology utilizing a non-zeolitic molecular sieve catalytic material, such as a metal aluminophosphate (ELAPO) molecular sieve. OTO and MTO processes, while useful, utilize an indirect process for forming a desired hydrocarbon product by first converting a feed to an oxygenate and subsequently converting the oxygenate to the hydrocarbon product. This indirect route of production is often associated with energy and cost penalties, often reducing the advantage gained by using a less expensive feed material.

Recently, attempts have been made to use pyrolysis to convert natural gas to ethylene. U.S. Pat. No. 7,183,451 discloses heating natural gas to a temperature at which a fraction is converted to hydrogen and a hydrocarbon product such as acetylene or ethylene. The product stream is then quenched to stop further reaction and subsequently reacted in the presence of a catalyst to form liquids to be transported. The liquids ultimately produced include naphtha, gasoline, or diesel.

While this method may be effective for converting a portion of natural gas to acetylene or ethylene, it is estimated that this approach will provide only about a 40% yield of acetylene from a methane feed stream. While it has been identified that higher temperatures in conjunction with short residence times can increase the yield, technical limitations prevent further improvement to this process in this regard.

While the foregoing traditional pyrolysis systems provide solutions for converting ethane and propane into other useful hydrocarbon products, they have proven either ineffective or uneconomical for converting methane into these other products, such as, for example ethylene. While MTO technology is promising, these processes can be expensive due to the indirect approach of forming the desired product. Due to continued increases in the price of feeds for traditional processes, such as ethane and naphtha, and the abundant supply and corresponding low cost of natural gas and other methane sources available, for example the more recent accessibility of shale gas, it is desirable to provide commer-

DETAILED DESCRIPTION

One proposed alternative to the previous methods of producing olefins that has not gained much commercial traction includes passing a hydrocarbon feedstock into a supersonic reactor and accelerating it to supersonic speed to provide kinetic energy that can be transformed into heat to enable an endothermic pyrolysis reaction to occur. Variations of this process are set out in U.S. Pat. No. 4,136,015; U.S. Pat. No. 4,724,272; and Russian Patent No. SU 392723A. These processes include combusting a feedstock or carrier fluid in an oxygen-rich environment to increase the temperature of the feed and accelerate the feed to supersonic speeds. A shock wave is created within the reactor to initiate pyrolysis or cracking of the feed.

More recently, U.S. Pat. No. 5,219,530 and U.S. Pat. No. 5,300,216 have suggested a similar process that utilizes a shock wave reactor to provide kinetic energy for initiating pyrolysis of natural gas to produce acetylene. More particularly, this process includes passing steam through a heater section to become superheated and accelerated to a nearly supersonic speed. The heated fluid is conveyed to a nozzle which acts to expand the carrier fluid to a supersonic speed and lower temperature. An ethane feedstock is passed through a compressor and heater and injected by nozzles to mix with the supersonic carrier fluid to turbulently mix together at a speed of about Mach 2.8 and a temperature of about 427° C. The temperature in the mixing section remains low enough to restrict premature pyrolysis. The shockwave reactor includes a pyrolysis section with a gradually increasing cross-sectional area where a standing shock wave is formed by back pressure in the reactor due to flow restriction at the outlet. The shock wave rapidly decreases the speed of the fluid, correspondingly rapidly increasing the temperature of the mixture by converting the kinetic energy into heat. This immediately initiates pyrolysis of the ethane feedstock to convert it to other products. A quench heat exchanger then receives the pyrolized mixture to quench the pyrolysis reaction.

Methods and apparatus for converting hydrocarbon components in methane feed streams using a supersonic reactor are generally disclosed. As used herein, the term "methane feed stream" includes any feed stream comprising methane. The methane feed streams provided for processing in the supersonic reactor generally include methane and form at least a portion of a process stream. The apparatus and methods presented herein convert at least a portion of the methane to a desired product hydrocarbon compound to produce a product stream having a higher concentration of the product hydrocarbon compound relative to the feed stream.

Figure 2:
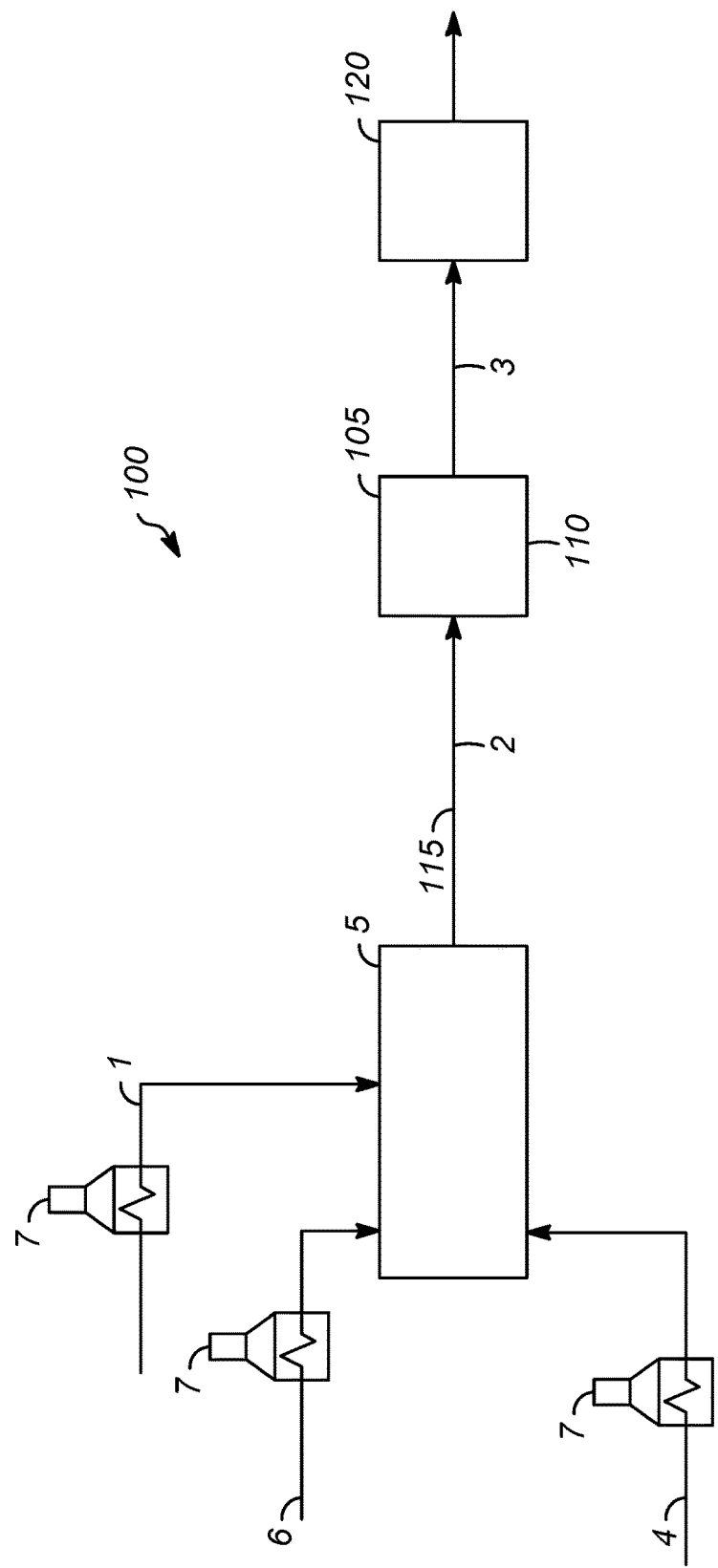
FIG. 2 is a schematic view of a system for converting methane into acetylene and other hydrocarbon products in accordance with various embodiments described herein.

The term "hydrocarbon stream" as used herein refers to one or more streams that provide at least a portion of the methane feed stream entering the supersonic reactor as described herein or are produced from the supersonic reactor from the methane feed stream, regardless of whether further treatment or processing is conducted on such hydrocarbon stream. With reference to the example illustrated in FIG. 2, the "hydrocarbon stream" may include the methane feed stream 1, a supersonic reactor effluent stream 2, a desired product stream 3 exiting a downstream hydrocarbon conversion process or any intermediate or by-product streams formed during the processes described herein. The hydrocarbon stream may be carried via a process stream line 115, as shown in FIG. 2, which includes lines for carrying each of the portions of the process stream described above. The term "process stream" as used herein includes the "hydrocarbon stream" as described above, as well as it may include a carrier fluid stream, a fuel stream 4, an oxygen source stream 6, or any streams used in the systems and the processes described herein. The process stream may be carried via a process stream line 115, which includes lines for carrying each of the portions of the process stream described above. As illustrated in FIG. 2, any of methane feed stream 1, fuel stream 4, and oxygen source stream 6, may be preheated, for example, by one or more heaters 7.

Prior attempts to convert light paraffin or alkane feed streams, including ethane and propane feed streams, to other hydrocarbons using supersonic flow reactors have shown promise in providing higher yields of desired products from a particular feed stream than other more traditional pyrolysis systems. Specifically, the ability of these types of processes to provide very high reaction temperatures with very short associated residence times offers significant improvement over traditional pyrolysis processes. It has more recently been realized that these processes may also be able to convert methane to acetylene and other useful hydrocarbons, whereas more traditional pyrolysis processes were incapable or inefficient for such conversions.

The majority of previous work with supersonic reactor systems, however, has been theoretical or research based, and thus has not addressed problems associated with practicing the process on a commercial scale. In addition, many of these prior disclosures do not contemplate using supersonic reactors to effectuate pyrolysis of a methane feed stream, and tend to focus primarily on the pyrolysis of ethane and propane. One problem that has recently been identified with adopting the use of a supersonic flow reactor for light alkane pyrolysis, and more specifically the pyrolysis of methane feeds to form acetylene and other useful products therefrom, includes the damaging effects that the severe operating conditions for pyrolysis of the methane can have on the supersonic flow reactor and other associated equipment. Previous work has not fully appreciated or addressed these severe operating conditions. For example, the supersonic reactor may operate at temperatures up to 3000° C. or higher, along with high pressures. These high temperatures and pressures pose a risk for mechanical failure within reactor walls of the reactor as a result of melting, rupture, or creep. Specifically, at elevated temperature, it has been identified that hot spots on the walls may indicate shell melting. In addition, even where the walls are cooled, chemically based damage may occur, such as, for example redox reactions forming non-passive products that are lost to the gas flow, causing recession. Further, translated oxidation may occur, creating non-adhering oxides that are lost to the gas flow.

In addition, a carrier stream and feed stream may travel through the reactor at supersonic speeds, which can quickly erode many materials that could be used to form the reactor shell. Moreover, certain substances and contaminants that may be present in the hydrocarbon stream can cause corrosion, oxidation, and/or reduction of the reactor walls or shell and other equipment or components of the reactor. Such components causing corrosion, oxidation, or reduction problems may include, for example hydrogen sulfide, water, methanethiol, arsine, mercury vapor, carbidization via reaction within the fuel itself, or hydrogen embrittlement. Another problem that may be present at high temperatures is reaction with transient species, such as radicals, e.g. hydroxide.

In accordance with various embodiments disclosed herein, therefore, apparatus and methods for converting methane in hydrocarbon streams to acetylene and other products are provided. Apparatus in accordance herewith, and the use thereof, have been identified to improve the overall process for the pyrolysis of light alkane feeds, including methane feeds, to acetylene and other useful products. The apparatus and processes described herein also improve the ability of the apparatus and associated components and equipment thereof to withstand degradation and possible failure due to extreme operating conditions within the reactor.

In accordance with one approach, the apparatus and methods disclosed herein are used to treat a hydrocarbon process stream to convert at least a portion of methane in the hydrocarbon process stream to acetylene. The hydrocarbon process stream described herein includes the methane feed stream provided to the system, which includes methane and may also include ethane or propane. The methane feed stream may also include combinations of methane, ethane, and propane at various concentrations and may also include other hydrocarbon compounds as well as contaminants. In one approach, the hydrocarbon feed stream includes natural gas. The natural gas may be provided from a variety of sources including, but not limited to, gas fields, oil fields, coal fields, fracking of shale fields, biomass, and landfill gas. In another approach, the methane feed stream can include a stream from another portion of a refinery or processing plant. For example, light alkanes, including methane, are often separated during processing of crude oil into various products and a methane feed stream may be provided from one of these sources. These streams may be provided from the same refinery or different refinery or from a refinery off gas. The methane feed stream may include a stream from combinations of different sources as well.

In accordance with the processes and systems described herein, a methane feed stream may be provided from a remote location or at the location or locations of the systems and methods described herein. For example, while the methane feed stream source may be located at the same refinery or processing plant where the processes and systems are carried out, such as from production from another on-site hydrocarbon conversion process or a local natural gas field, the methane feed stream may be provided from a remote source via pipelines or other transportation methods. For example a feed stream may be provided from a remote hydrocarbon processing plant or refinery or a remote natural gas field, and provided as a feed to the systems and processes described herein. Initial processing of a methane stream may occur at the remote source to remove certain contaminants from the methane feed stream. Where such initial processing occurs, it may be considered part of the systems and processes described herein, or it may occur upstream of the systems and processes described herein. Thus, the methane feed stream provided for the systems and processes described herein may have varying levels of contaminants depending on whether initial processing occurs upstream thereof.

In one example, the methane feed stream has a methane content ranging from about 65 mol-% to about 100 mol-%. In another example, the concentration of methane in the hydrocarbon feed ranges from about 80 mol-% to about 100 mol-% of the hydrocarbon feed. In yet another example, the concentration of methane ranges from about 90 mol-% to about 100 mol-% of the hydrocarbon feed.

In one example, the concentration of ethane in the methane feed stream ranges from about 0 mol-% to about 35 mol-% and in another example from about 0 mol-% to about 10 mol-%. In one example, the concentration of propane in the methane feed ranges from about 0 mol-% to about 5 mol-% and in another example from about 0 mol-% to about 1 mol-%.

The methane feed stream may also include heavy hydrocarbons, such as aromatics, paraffinic, olefinic, and naphthenic hydrocarbons. These heavy hydrocarbons if present will likely be present at concentrations of between about 0 mol-% and about 100 mol-%. In another example, they may be present at concentrations of between about 0 mol-% and 10 mol-% and may be present at between about 0 mol-% and 2 mol-%.

The apparatus and method for forming acetylene from the methane feed stream described herein utilizes a supersonic flow reactor for pyrolyzing methane in the feed stream to form acetylene. The supersonic flow reactor may include one or more reactors capable of creating a supersonic flow of a carrier fluid and the methane feed stream and expanding the carrier fluid to initiate the pyrolysis reaction. In one approach, the process may include a supersonic reactor as generally described in U.S. Pat. No. 4,724,272, which is incorporated herein by reference, in its entirety. In another approach, the process and system may include a supersonic reactor such as described as a "shock wave" reactor in U.S. Pat. No. 5,219,530 and U.S. Pat. No. 5,300,216, which are incorporated herein by reference, in their entirety. In yet another approach, the supersonic reactor described as a "shock wave" reactor may include a reactor such as described in "Supersonic Injection and Mixing in the Shock Wave Reactor" Robert G. Cerff, University of Washington Graduate School, 2010.

Figure 1:
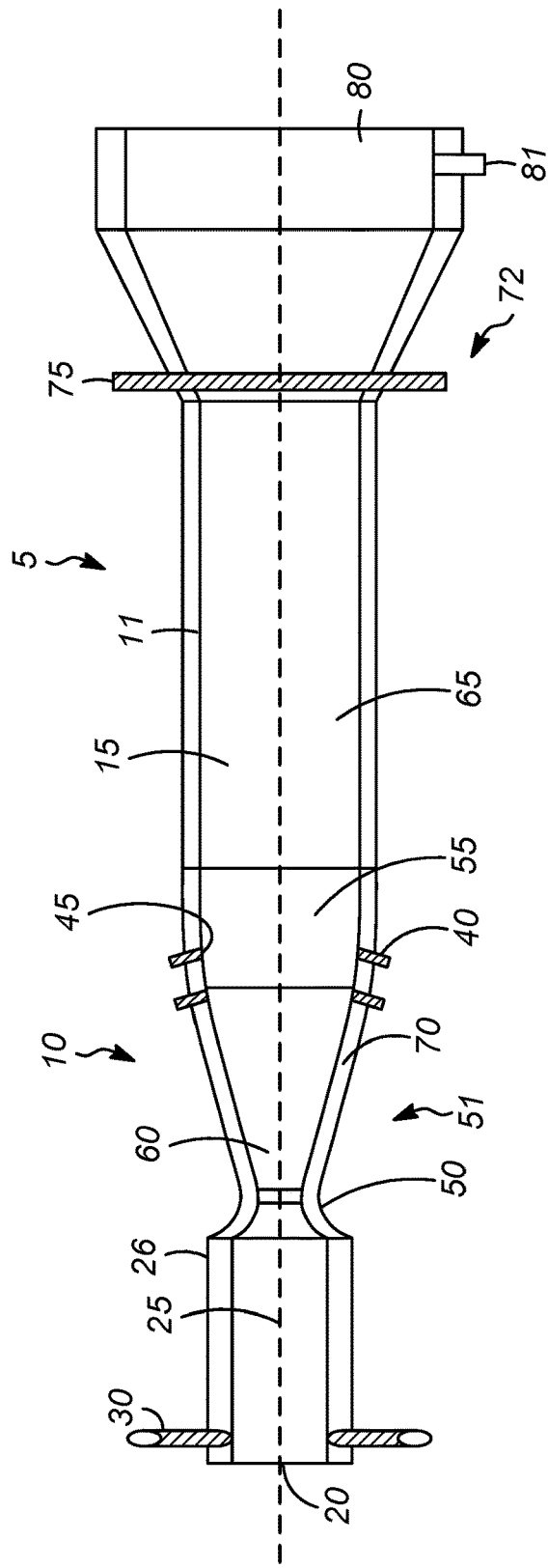
FIG. 1 is a side cross-sectional view of a supersonic reactor in accordance with various embodiments described herein.

While a variety of supersonic reactors may be used in the present process, an exemplary reactor 5 is illustrated in FIG. 1. Referring to FIG. 1, the supersonic reactor 5 includes a reactor vessel 10 generally defining a reactor chamber 15. While the reactor 5 is illustrated as a single reactor, it should be understood that it may be formed modularly or as separate vessels. If formed modularly or as separate components, the modules or separate components of the reactor may be joined together permanently or temporarily, or may be separate from one another with fluids contained by other means, such as, for example, differential pressure adjustment between them. A combustion zone or chamber 25 is provided for combusting a fuel to produce a carrier fluid with the desired temperature and flowrate. The reactor 5 may optionally include a carrier fluid inlet 20 for introducing a supplemental carrier fluid into the reactor. One or more fuel injectors 30 are provided for injecting a combustible fuel, for example hydrogen, into the combustion chamber 26. The same or other injectors may be provided for injecting an oxygen source into the combustion chamber 26 to facilitate combustion of the fuel. The fuel and oxygen source injection may be in an axial direction, tangential direction, radial direction, or other direction, including a combination of directions. The fuel and oxygen are combusted to produce a hot carrier fluid stream typically having a temperature of from about 1200° to about 3500° C. in one example, between about 2000° and about 3500° C. in another example, and between about 2500° and about 3200° C. in yet another example. It is also contemplated herein to produce the hot carrier fluid stream by other known methods, including non-combustion methods. According to one example the carrier fluid stream has a pressure of about 1 atm or higher, greater than about 2 atm in another example, and greater than about 4 atm in another example.

The hot carrier fluid stream from the combustion zone 25 is passed through a supersonic expander 51 that includes a converging-diverging nozzle 50 to accelerate the velocity of the carrier fluid to above about Mach 1.0 in one example, between about Mach 1.0 and Mach 4.0 in another example, and between about Mach 1.5 and 3.5 in another example. In this regard, the residence time of the fluid in the reactor portion of the supersonic flow reactor is between about 0.5 and 100 ms in one example, about 1.0 and 50 ms in another example, and about 1.5 and 20 ms in another example. The temperature of the carrier fluid stream through the supersonic expander by one example is between about 1000° C. and about 3500° C., between about 1200° C. and about 2500° C. in another example, and between about 1200° C. and about 2000° C. in another example.

A feedstock inlet 40 is provided for injecting the methane feed stream into the reactor 5 to mix with the carrier fluid. The feedstock inlet 40 may include one or more injectors 45 for injecting the feedstock into the nozzle 50, a mixing zone 55, a diffuser zone 60, or a reaction zone or chamber 65. The injector 45 may include a manifold, including for example a plurality of injection ports or nozzles for injecting the feed into the reactor 5.

In one approach, the reactor 5 may include a mixing zone 55 for mixing of the carrier fluid and the feed stream. In one approach, as illustrated in FIG. 1, the reactor 5 may have a separate mixing zone, between for example the supersonic expander 51 and the diffuser zone 60, while in another approach, the mixing zone is integrated into the diffuser section, and mixing may occur in the nozzle 50, expansion zone 60, or reaction zone 65 of the reactor 5. An expansion zone 60 includes a diverging wall 70 to produce a rapid reduction in the velocity of the gases flowing therethrough, to convert the kinetic energy of the flowing fluid to thermal energy to further heat the stream to cause pyrolysis of the methane in the feed, which may occur in the expansion section 60 and/or a downstream reaction section 65 of the reactor. The fluid is quickly quenched in a quench zone 72 to stop the pyrolysis reaction from further conversion of the desired acetylene product to other compounds. Spray bars 75 may be used to introduce a quenching fluid, for example water or steam into the quench zone 72.

The reactor effluent exits the reactor via outlet 80 and as mentioned above forms a portion of the hydrocarbon stream. The effluent will include a larger concentration of acetylene than the feed stream and a reduced concentration of methane relative to the feed stream. The reactor effluent stream may also be referred to herein as an acetylene stream as it includes an increased concentration of acetylene. The acetylene stream may be an intermediate stream in a process to form another hydrocarbon product or it may be further processed and captured as an acetylene product stream. In one example, the reactor effluent stream has an acetylene concentration prior to the addition of quenching fluid ranging from about 2 mol-% to about 30 mol-%. In another example, the concentration of acetylene ranges from about 5 mol-% to about 25 mol-% and from about 8 mol-% to about 23 mol-% in another example.

The reactor vessel 10 includes a reactor shell 11. It should be noted that the term "reactor shell" refers to the wall or walls forming the reactor vessel, which defines the reactor chamber 15. The reactor shell 11 will typically be an annular structure defining a generally hollow central reactor chamber 15. The reactor shell 11 may include a single layer of material, a single composite structure or multiple shells with one or more shells positioned within one or more other shells. The reactor shell 11 also includes various zones, components, and or modules, as described above and further described below for the different zones, components, and or modules of the supersonic reactor 5. The reactor shell 11 may be formed as a single piece defining all of the various reactor zones and components or it may be modular, with different modules defining the different reactor zones and/or components.

By one approach, one or more portions of the reactor wall or shell 11 are formed as a casting. In this regard, the one or more portions may not be formed by welding or forming or other manufacturing methods, although additional treating may be performed on the casting as described below. Without intending to be bound by theory, it is believed that because welds often include residual stress, forming the reactor wall or walls by welding may yield a reactor that is more susceptible to failure or rupture under high temperatures and pressures. In addition, due to their varying microstructure and possible composition gradients, welds may also be more susceptible to corrosion and cracking. Similarly, it is believed that forming the reactor walls would result in non-negligible residual stresses formed in the reactor walls, causing similar problems with operation at high temperatures and pressures. Thus, by forming a portion of the reactor shell as a casting, a more isotropic microstructure is provided. The cast portion of the reactor shell may provide corrosion resistance over similar components formed by other methods, such as welding or forming. Forming the reactor shell from a casting may also provide more uniform heat flux and more uniform temperatures in the component. Forming the portion of the reactor shell from a casting may also provide better and more uniform high temperature creep and failure resistance than forming the shell by other methods.

By one approach, the casting may include a directional casting to provide improved thermal shock resistance and creep resistance at the elevated reaction temperatures and pressures. In one approach, the casting includes a columnar grain structure. In another approach, the casting includes a single crystal structure.

The casting may be formed from one or more materials as described further below. The cast portion of the reactor may be further treated by various methods known in the art. For example, the cast reactor shell 11 may be coated, as further described herein, heat treated, tempered, carbided, nitride, or treated in other known methods to improve its properties.

A single casting may be used to form the entire reactor shell 11, or the reactor shell 11 may include individually cast components or modules, as described further herein, that are assembled to form the reactor shell 11. Further, where the reactor shell 11 includes various layers, including coatings, inner and outer shells, etc., as further described herein, these layers may be cast separately or together, and subsequently maintained separately or joined together.

According to various other approaches, one or more portions of the supersonic reactor shell may be formed by known methods other than casting, such as, for example powder metallurgy, which may be densified by hot isostatic pressing, hipping a powder to a substrate, or laser sintering, or other suitable sintering methods, or machining from a billet.

By one approach, at least a portion of the reactor shell 11 is constructed of a material having a high melting temperature to withstand the high operating temperatures of the supersonic reactor 5. In one approach, one or more materials forming the portion of the reactor shell 11 may have a long low-cycle fatigue life, high yield strength, resistance to creep and stress rupture, oxidation resistance, and compatibility with coolants and fuels. In one example, at least a portion of the reactor shell 11 is formed of a material having a melting temperature of between about 1200° and about 4000° C., and in another example from about 1800° to about 3500° C. The materials may also exhibit microstructural stability through diverse thermal and mechanical processing procedures, compatibility with bonding processes and good adherence of oxidation resistant coatings. Some preferred materials for forming at least a portion of the reactor shell include superalloys and nickel and gamma Ti aluminides. By one approach, the superalloy it is a nickel based superalloy, and by another approach, the superalloy is an iron based superalloy.

In one approach, the reactor shell 11 or wall portion is formed from a superalloy. In this regard, the wall may provide excellent mechanical strength and creep resistance at combustion and pyrolysis temperatures occurring within the reactor. In this manner, the apparatus may also restrict melting or failure due to the operating temperature and pressures in the reactor chamber 15.

According to another approach, the portion of the reactor shell 11 is formed from a material selected from the group consisting of a carbide, a nitride, titanium diboride, a sialon ceramic, zirconia, thoria, a carbon-carbon composite, tungsten, tantalum, molybdenum, chromium, nickel and alloys thereof.

According to yet another approach, the portion of the reactor shell 11 is formed as a casting wherein the casting comprises a component selected from the group consisting of duplex stainless steel, super duplex stainless steel, and nickel-based high-temperature low creep superalloy.

Chromium or nickel may be included to provide good corrosion resistance.

By another aspect, the reactor walls are constructed of a material having high thermal conductivity. In this manner, heat from reactor chamber 15 may be quickly removed therefrom.

This may restrict a skin temperature of an internal surface of the reactor shell 11 from being heated to temperatures at or near the reactor temperature, which may cause melting, chemical fire, or other deterioration, to the reactor shell 11 walls. In one example, the one or more portions of the reactor are formed from a material having a thermal conductivity of between about 200 and about 500 W/m-K. In another example, the thermal conductivity is between about 300 and about 450 W/m-K. In yet another example, the thermal conductivity is between about 200 and about 346 W/m-K and may be between about 325 and about 375 W/m-K in yet another example.

It has been found that according to this approach, the reactor shell may be formed from a material having a relatively low melting temperature as long as the material has a very high conductivity. Because heat from the reaction chamber 15 is quickly removed in this approach, the reactor shell 11 is not exposed to as high as the temperature. In this regard, by forming the reactor shell portion from a material having a high thermal conductivity, the material may have a melting temperature below the temperature in the reactor chamber 15. In one example, the portion of the reactor shell 11 is formed from a material having a melting temperature of between about 500° and about 2000° C. In another example, the reactor shell 11 portion may be formed from a material having a melting temperature of between about 800° and about 1300° C. and may be formed from a material having a melting temperature of between about 1000° and about 1200° C. in another example.

By one approach, the material having a high thermal conductivity includes a metal or metal alloy. In one approach, one or more portions of the reactor shell 11 may be formed from copper, silver, aluminum, zirconium, niobium, and their alloys. In this regard, it should be noted that one or more of the materials listed above may also be used to form a coating on a reactor shell substrate or to form a layer of a multilayer reactor shell 11. By one approach, the reactor shell 11 portion includes copper or a copper alloy. In one example, the reactor shell portion includes a material selected from the group consisting of copper chrome, copper chrome zinc, copper chrome niobium, copper nickel and copper nickel tungsten. In another example, the reactor shell portion comprises niobium-silver. In order to enhance the removal of heat from reactor chamber, cooling may be used to more quickly remove the heat from the reactor chamber so that a temperature thereof is maintained below and allowable temperature.

Figure 3:
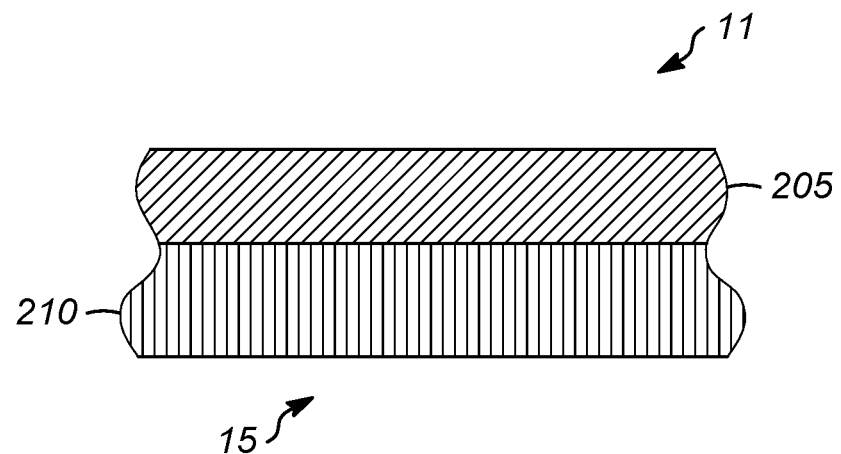
FIG. 3 is a partial side cross-sectional view showing portions of the supersonic reactor of FIG. 1 in accordance with various embodiments described herein.
Figure 8:
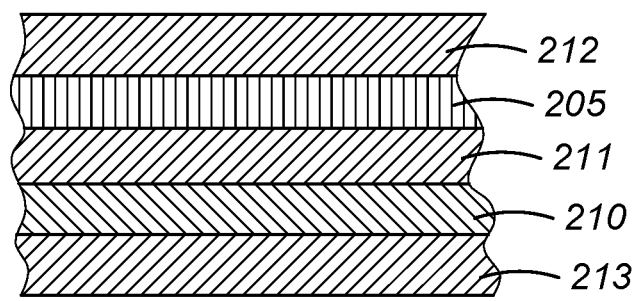
FIG. 8 is a partial side cross-sectional view showing portions of the supersonic reactor of FIG. 1 in accordance with various embodiments described herein.

By another approach, the reactor shell 11 may include a plurality of layers. The reactor shell 11 illustrated in FIG. 3 includes an inner layer 210 defining the reactor chamber 15 and an outer layer 205 formed about the inner 210. While the reactor shell 11 illustrated in FIG. 3 has two layers for ease of explanation, as illustrated in FIG. 8, it should be understood that the reactor shell 11 may include three or more layers having one or more intermediate layers 211 between the inner layer 210 and the outer layer 205. Further, one or more additional outer layers 212 may be positioned outside of outer layer 212. One or more additional inner layers may be positioned inside of inner layer 210.

In one approach, the inner layer 210 includes a coating that is formed on an inner surface of the outer layer 205 or any intervening intermediate layers 211. In this regard, the outer layer 205 forms a substrate on which the inner layer 210 coating is applied. Alternatively, the inner layers 210 may provide a substrate on which an outer layer 205 coating is applied. One or both of the inner layer 210 and the outer layer 205 may be formed as a casting as described previously or formed in other known manners in accordance with this approach.

In one approach, at least a portion of the inner layer 210 includes a high melting temperature material as described above. According to another approach, the inner layer 210 includes a material selected from the group consisting of a carbide, a nitride, titanium diboride, a sialon ceramic, zirconia, thoria, a carbon-carbon composite, tungsten, tantalum, molybdenum, chromium, nickel and alloys thereof. By yet another approach, the inner layer 210 includes a superalloy, and by another approach includes a material selected from the group consisting of duplex stainless steel, super duplex stainless steel, and nickel-based high-temperature low creep superalloy. In this regard, the inner layer 210 may be selected to provide beneficial operating characteristics, particularly as it is exposed to the harsh operating conditions within the reactor chamber 15, including the high temperature thereof.

In another approach, at least a portion of the inner layer 210 includes a high thermal conductivity material as described above. According to another approach, the inner layer 210 includes a material selected from the group consisting of copper, silver, aluminum, zirconium, niobium, and alloys thereof. By yet another approach, the inner layer 210 includes a material selected from the group consisting of copper chrome, copper chrome zinc, copper chrome niobium, copper nickel and copper nickel tungsten. In another example, the reactor shell portion comprises niobium-silver. In this regard, the inner layer 210 may be selected to provide beneficial operating characteristics, particularly as it is exposed to the harsh operating conditions within the reactor chamber 15, including the high temperature thereof.

In one approach, the outer layer 205 may be formed of a different material than the inner layer 210. The outer layer 205 material may be selected to provide structural support or other desirable properties to the reactor shell 11. In one example, the outer layer 205 or an intermediate layer includes corrosion resistant steel. Other suitable materials for forming the outer layer 205 of the reactor shell 11 include, but are not limited to, duplex stainless steel, super duplex stainless steel, and nickel-based high-temperature low creep superalloy, Nimonic™ nickel-based high-temperature low creep superalloy, Inco™ 718, Haynes™, 230, or other nickel alloys such as Mar-M-247.

In one approach, the inner layer 210 includes a thermal barrier coating. Thermal barrier coatings may be formed from a material that exhibits desirable properties for use in the reactor chamber 15 such as, for example, high melting temperature to withstand the high temperatures in the reactor chamber 15. For example, the thermal barrier coating may include Yttria-stabilized zirconia, lanthanum and rare earth-doped lanthanum hexaluminate, hafnium carbide or tungsten, as both materials have high melting temperatures, good mechanical properties at high operating temperatures, and optionally low thermal conductivity.

In one approach, a bond coat is provided between the inner layer 210 and the surface of the outer layer 205, including the thermal barrier coating by one approach. The bond coat may include, NiCrAlY, NiCoCrAlY alloys that are applied on the metal surface by plasma spray, electron beam PVD, or other methods known in the art. Other bond coatings for copper alloys may include NiAl applied by low pressure, vacuum plasma spray, or other methods known in the art.

The layered reactor shell 11 may be formed in any known manner known in the art. In one approach, an internal diameter coating formed on a mandrel may be used to provide a layered reactor shell by providing a coating on a substrate material. By another approach, a coating may be formed on a substrate by hot isostatic pressing to provide the layered reactor shell 11. By yet another approach, cladding may be used to provide a coating on a substrate. In still another approach, the inner layer and outer layers may be separately formed and joined together. An example of this approach includes separately casting the inner layer 210 and the outer layer 205 and brazing them together to form the layered reactor shell 11. Bi-casting may also be used by casting a second alloy about a first alloy.

Figure 4:
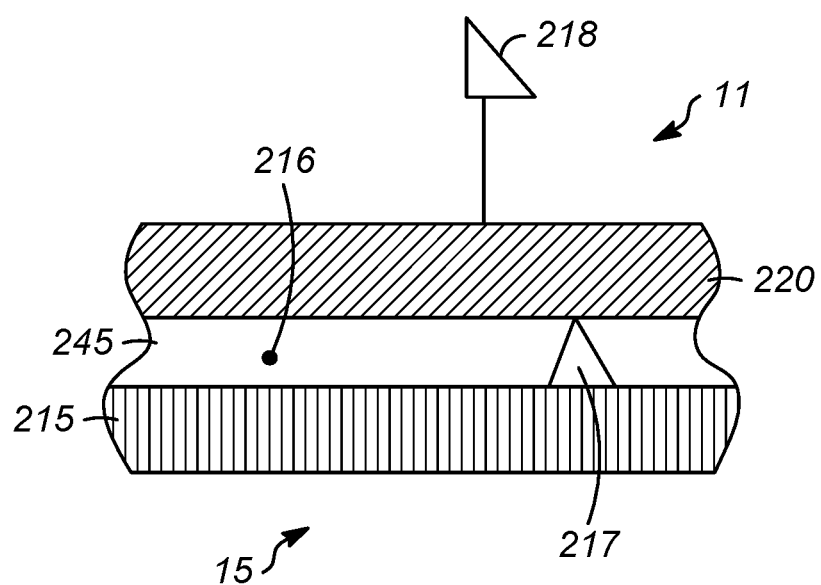
FIG. 4 is a partial side cross-sectional view showing portions of the supersonic reactor of FIG. 1 in accordance with various embodiments described herein.

In another approach, as illustrated in FIG. 4, at least a portion of the reactor shell 11 may include a separate inner shell 215 and outer shell 220. Similar to the layered reactor shell 11 described previously, a reactor shell having a separate inner shell 215 and outer shell 220 may allow the inner shell 215 to withstand the operating conditions of the reactor chamber 15 while the outer shell 220 provides structural support and/or other desirable properties to the reactor shell 11.

In one approach, at least a portion of the inner shell 215 includes the high melting temperature material as described above. According to another approach, at least a portion of the inner shell 215 includes a material selected from the group consisting of a carbide, a nitride, titanium diboride, a sialon ceramic, zirconia, thoria, a carbon-carbon composite, tungsten, tantalum, molybdenum, chromium, nickel and alloys thereof. By yet another approach, at least a portion of the inner shell 210 includes a superalloy and by another approach includes a material selected from the group consisting of duplex stainless steel, super duplex stainless steel, and nickel-based high-temperature low creep superalloy. In this regard, the inner shell 215 may be selected to provide beneficial operating characteristics, particularly as it is exposed to the harsh operating conditions within the reactor chamber 15.

In another approach, at least a portion of the inner shell 215 includes a high thermal conductivity material as described above. According to another approach, the inner shell 215 includes a material selected from the group consisting of copper, silver, aluminum, zirconium, niobium, and alloys thereof. By yet another approach, the inner shell 215 includes a material selected from the group consisting of copper chrome, copper chrome zinc, copper chrome niobium, copper nickel and copper nickel tungsten. In another example, the inner shell 215 comprises niobium-silver. In another approach the inner shell may include a material comprising a copper alloy that has been precipitation hardened with second phase compounds that alloy the retention of high thermal conductivity. In this regard, the inner shell 215 may be selected to provide beneficial operating characteristics, particularly as it is exposed to the harsh operating conditions within the reactor chamber 15, including the high temperature thereof.

In one approach, the outer shell 220 may be formed of a different material than the inner shell 215. The outer shell 220 may be selected to provide structural support or other desirable properties to the reactor shell 11. In one example, the outer shell 220 includes corrosion resistant steel. Other suitable materials for forming the outer layer 205 of the reactor shell 11 include, but are not limited to, duplex stainless steel, super duplex stainless steel, and nickel-based high-temperature low creep superalloy, Nimonic™ nickel-based high-temperature low creep superalloy, Inco™ 718, Haynes™, 230, or other nickel alloys such as Mar-M-247.

By one approach, one or both of the inner shell 215 and the outer shell 220 is formed as a casting as described previously.

Figure 5:
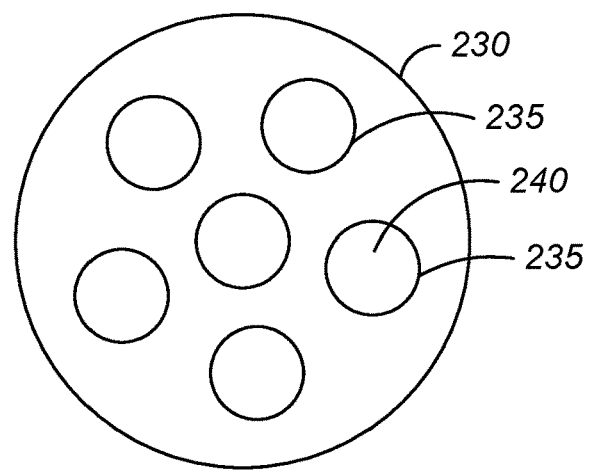
FIG. 5 is a cross-sectional view showing a supersonic reactor in accordance with various embodiments described herein.

In one approach, the outer shell 220 includes a tube sheet 230 as illustrated in FIG. 5. According to this approach, at least one additional inner shell 235 is positioned inside the outer shell 230 defining a second reactor chamber 240. In this manner, a plurality of pyrolysis reactions may occur within the plurality of reactor chambers 240. By this approach, each of the inner shells 235 may include some or all of the components described above with regard to supersonic reactor 5 illustrated in FIG. 1, or some components of the separate inner shells 235 may be integrated. In one approach, some the inner reactor shells 235 may be orientated in opposite directions. In this regard, any thrust that may be generated by the high speed streams flowing through the inner shells will be offset by oppositely facing inner reactor shells 235.

In one approach, the inner shell 215 is spaced from the outer shell 220 to provide a channel 245 therebetween as illustrated in FIG. 4. In this approach, the channel 245 may include a pressure zone. The pressure zone is pressurized to maintain the pressure therein at about the same pressure as the reactor chamber 15 pressure. In this regard, the inner shell 215 may be configured such that it does not have to withstand a high pressure differential between its inner surface 250 and outer surface 255. The inner shell 215 may then be formed of a material having a relatively lower pressure rating and/or having a relatively thin wall thickness. The outer shell 220 may then provide structural support as well as serving as a pressure vessel to withstand the pressure differential between the pressure zone 245 and the outside of the outer shell 220. In another approach (not shown), the inner shell 215 may abut the outer shell 220.

In one approach, channel 245 further houses one or more sensors 216. The sensors may detect or measure a variable such as one or more parameters or materials within channel 245. Examples of sensors include pressure sensors, temperature sensors, chemical sensors such as gas sensors, hydrogen sensors, hydrocarbon sensors, methane sensors, and others. The sensors may be electronically connected to one or more display, monitoring and or control systems. In one approach channel 245 further houses one or more support structures 217 to support inner shell 215 relative to outer shell 220.

Figure 6:
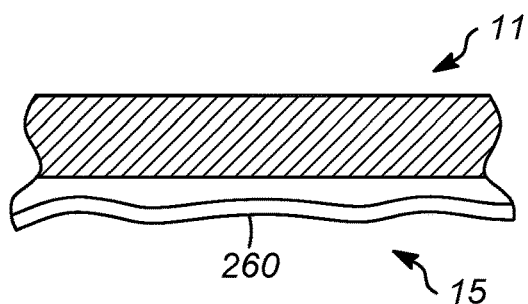
FIG. 6 is a partial side cross-sectional view showing portions of the supersonic reactor of FIG. 1 in accordance with various embodiments described herein.

According to another approach, as illustrated in FIG. 6, a liner 260 may be provided inside at least a portion of the reactor shell 11 to resist deterioration of the reactor shell 11 portion due to operating conditions within the reactor chamber 15. The liner 260 may extend along an internal surface of the reactor shell 11 and may abut the reactor shell 11 or be spaced therefrom.

In one approach, a liner 260 includes a disposable liner. The disposable liner may comprise carbon in the form of carbon/carbon composite, pyrolytic carbon, glassy carbon, or other forms of carbon or a high temperature alloy and may be removed and replaced after deterioration of the liner 260 has occurred. In this regard, the disposable liner may protect the reactor shell from the harsh operating conditions within the reactor chamber 15.

According to another approach, the liner 260 includes a self-regenerating liner, and is able to regenerate during operation of the supersonic reactor 5 and/or when the supersonic reactor 5 is taken offline. In one approach, the self-regenerating liner includes carbon that is catalyzed to promote carbon or coke formation along the internal surface of the reactor shell 11 to regenerate the carbon liner. In another approach, the self regenerating liner includes a self-regenerating lining having a graphitic layer of coke. In another approach, the self-regenerating liner includes a lining having a nanostructured layer of coke. In yet another approach, the self-regenerating liner includes a lining with a nanostructured layer of graphene. In one approach, the self-regenerating liner includes directional thermal conductivity too quickly remove heat from the reaction chamber 15 during operation.

In one approach, the liner 260 includes a low thermal conductivity coating which operates to provide protection for the metal alloys used, and slow down heat transfer. In another approach, the liner may be a floating captured liner made from high temperature resistance, low thermal conductivity materials. Such a liner would reduce heat transfer and erosion. A floating captured liner may be formed by vacuum plasma spray of an HfC or rhenium onto a suitable mandrel machined to the net shape dimensions of the required liner outer diameter. The spray coating of the HfC or rhenium would be followed by a tungsten structural layer capable of supporting the structure at the necessary temperatures. The tungsten layer would be followed by molybdenum and possibly another tungsten and or a nickel, cobalt, chromium, aluminum yttrium structural layer. All layers would be applied using vacuum plasma spray and will stand alone after the inner diameter of the mandrel is chemically etched.

Figure 7:
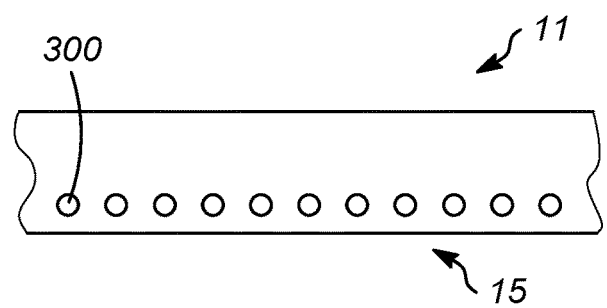
FIG. 7 is a partial side cross-sectional view showing portions of the supersonic reactor of FIG. 1 in accordance with various embodiments described herein.

In one approach, one or more portions of the reactor shell 11 include active cooling to dissipate heat from the reactor chamber 15 and restrict melting or other deterioration of the reactor shell 11 due to high temperatures and other operating conditions. In one approach, the active cooling includes an active cooling system. As illustrated in FIG. 7, a cross-section of a portion of the reactor shell 11 is illustrated showing an active cooling system that includes a plurality of cooling passageways 300 formed in the reactor shell 11 to flow a coolant along the reactor shell 11 to remove heat therefrom. The active cooling system may also include a coolant source for providing pressurized coolant passing through the cooling passageways 300. As illustrated in FIG. 7, the cooling passageways may extend generally circumferentially about the reactor shell 11, which in one approach includes a generally annular configuration. Manifold tubes may also be present for providing coolant to and from the cooling passageways 300.

Figure 9:
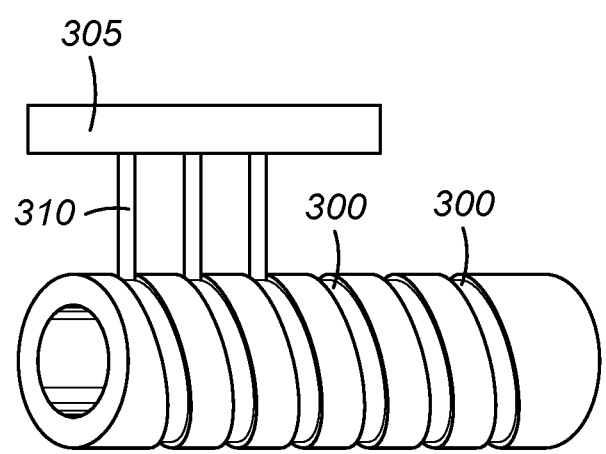
FIG. 9 is a perspective view of a portion of the supersonic reactor of FIG. 1.

In one approach, the cooling passageways 300 may include one or a plurality of channels formed in a surface of the reactor shell. In another approach, the cooling passageways 300 may include one or a plurality of tubes or generally hollow tunnels formed in the reactor shell 11 for flowing the cooling fluid therethrough, as in the illustrated form in FIG. 7. The passageways 300 may extend along one or more surfaces of the reactor or they may be formed within the walls of the reactor shell 11 as illustrated in FIG. 9. The passageways 300 may be provided in a variety of orientations and may extend axially along the reactor shell 11, circumferentially about the reactor shell 11, radially through the reactor shell, helically about the annular reactor shell or other orientations known in the art.

Figure 10:
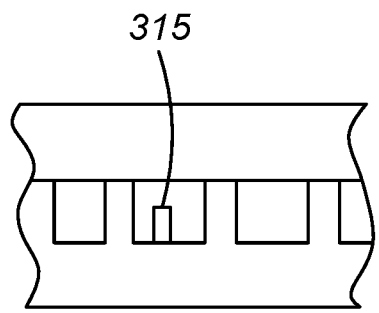
FIG. 10 is a partial side cross-sectional view showing portions of the supersonic reactor of FIG. 1 in accordance with various embodiments described herein.

In yet another approach, the cooling passageways 300 may include one or more spaces between inner and outer layers, linings, or inner and outer shells, as described previously, to provide one or more cooling channels, such as in channel 245 of FIG. 4. In addition, a flow manipulator may be provided within the space between inner and outer layers, linings or shells to direct cooling fluid along a desired flow pattern. As illustrated in FIG. 10, protrusions 315, such as pins, fins, or other protrusions, may be used within the space between inner and outer layers to increase surface area for cooling. Further, the cooling system may include a combination of different types of cooling passageways 300 as described herein. For example, the cooling passageways 300 may include a cooling channel 300 between layers 215 and 220 of a reactor shell 11 along with channels formed in a surface of one of the inner layer 215 and outer layer 220 such that coolant flowing through the cooling channels also passes through the reactor shell channels 245.

Cooling passageways 300 may be formed by a variety of methods. In one approach, cooling passageways 300 are machined into the reactor shell. In another approach, partial passageways may be formed along surface(s) of one or more layers, or shells, of a reactor shell 11 as described above, and a complete passageways 300 may be formed between the layers or shells upon joining the layers and and/or shells together as shown in FIG. 10. Similarly, a partial passageway may be formed on a surface of a reactor wall or layer and a coating or liner may be applied over the partial passageway to provide a complete passageway 300 between the reactor wall or layer and the coating or liner. In yet another approach, a coating or liner may be applied in a pattern defining a complete or partial passageway. Such partial or complete passageways may be formed as described above by machining, casting, or during application of a particular coating, layer or liner, or by other means. Cooling passageways 300 may also be formed by other methods as is generally known in the art. Pins, fins, or other protrusions may be used within the passageways to increase surface area for cooling. A low thermal conductivity coating may be applied to a liner, the coating operating to provide protection for the metal alloys used, and slow down heat transfer to the active cooling and increasing efficiency. By way of example, the coating may be a nickel or copper alloy that is vacuum plasma sprayed onto the inner lining first starting with a bond coating which allows adhesion of the structural metal to the low thermal conductivity material. The bond coating may contain nickel, chromium, cobalt, aluminum, and or yttrium, followed by molybdenum and tungsten, and finally followed by HfC or HfO2.

The walls that define the cooling passageways may aid in heat transfer into the circulated coolant by serving as cooling fins and also support coolant pressure loads. In one approach, the thickness of the hot gas wall (the portion of the reactor shell 11 wall between the coolant and the hot combustion gas) is optimized to minimize the resistance to heat flow through the walls of the liners and into the coolant channels 300 while providing structural integrity relative to the pressure and thermal loads. In one approach, the thickness of the hot gas wall is between about 0.10 inch and about 0.375 inch, and in another example is between about 0.15 inch and about 0.225 inch. In another approach the walls between cooling passages are optimized as fins to provide low thermal resistance from the hot wall to the coolant as well as maintain structural integrity.

In another approach, the coolant passages contain flow enhancers to enhance the flow of coolant to increase the coolant heat transfer coefficient and heat flux from the wall to the coolant. In one approach, the flow enhancers contain ribs oriented perpendicular or at a lesser angle to the coolant flow direction to re-start the coolant boundary layer, increasing the coolant heat transfer coefficient and increasing heat flux from the wall into the coolant. Swirl imparted by ribs positioned at an angle less than 90 degrees will impart a swirl velocity component, mixing the coolant and causing a higher heat transfer rate from the wall to the coolant.

When the reactor shell 11 is assembled, the manifold tubes and the network of coolant channels 300 cooperate to form a manifold for the flowing coolant to remove the heat generated during the combustion process in the supersonic reactor 5 to the extent needed to maintain an acceptable reactor wall temperature.

In one approach, the cooling fluid is pressurized to a relatively high pressure such that coolant flowing through portion of the reactor shell 11 has a pressure of between about 350 psig and about 3200 psig, and in another approach between about 1000 psig and about 2000 psig. And in another approach between about 1500 and about 1600 psig. The relatively high pressure reduces the complexity of the coolant circulation by avoiding a phase change when using, for example, water as the cooling fluid. The coolant pressure, circulation rate, and temperature are set to provide sufficient coolant flow to sufficiently remove a portion of the heat generated in the reactor chamber 15 to maintain an acceptable reactor wall temperature, particularly during combustion of the fuel stream and supersonic expansion. In one approach, the coolant has a flowrate through the coolant passageways of between about 28,000 pph and about 47,000 pph, and in another example between about 33,500 pph and about 80,000 pph. In one example, coolant has an inlet temperature of between about 50° F. to about 250° F. and in another example between about 85° F. to about 150° F. In one example, coolant has an outlet temperature of about 100° F. to about 700° F. and in another example, from about 250° F. to about 600° F. A variety of coolants known in the art may be used. In one example, the coolant includes water. In another example the coolant includes, steam, hydrogen or methane, and may contain a mixture of fluids.

In one approach, impingement cooling may be employed as the active cooling to dissipate heat from the reactor chamber 15 and restrict melting or other deterioration of the reactor shell 11 due to high temperatures and other operating conditions. Impingement cooling may employ a gas or a liquid. In one approach the impingement cooling may employ a series of impingement jets to affect high heat transfer. For example, a high velocity jets may be directed onto a shell to be cooled. As the cooling jet contacts the surface of the shell it is diverted in all directions parallel to the shell surface. The jets may be arranged about the shell, such as randomly or in a pattern. Impingement cooling may include techniques such as high impingement systems using vapor expansion for hot wall cooling, liquid wall impingement, and gas effusion cooling.

In one approach, a heat pipe may serve as the active cooling mechanism. Heat pipes can conduct up to 250 times the thermal energy of a solid copper conducting member.

Figure 12:
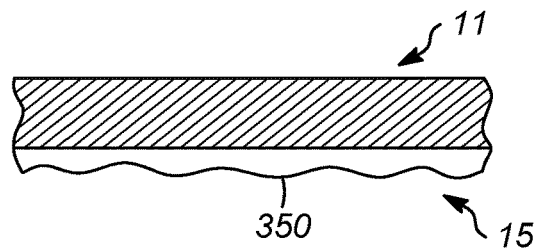
FIG. 12 is a partial side cross-sectional view showing portions of the supersonic reactor of FIG. 1 in accordance with various embodiments described herein.

In one approach, as illustrated in FIG. 12, a film barrier 350 may be provided along an inner surface of at least a portion of the reactor shell 11 to provide at least a partial barrier to the reactor chamber 15. The film barrier 350 may assist in restricting deterioration, including melting, erosion, or corrosion, of the reactor shell 11 due to the high temperatures, flowrates, and other harsh conditions within the reactor chamber 15.

In one approach, the film barrier 350 includes a cold fluid barrier. As used herein, cold fluid barrier refers to the temperature of the fluid barrier relative to the temperature in the reactor chamber 15. Thus, the cold fluid barrier may have a high temperature, but be cool relative to the rector chamber 15. In one example, the temperature of the cold fluid barrier is between about 3000° F. and about 5000° F. In another example, the temperature of the cold fluid barrier is between about 3600° and about 4600° F.

The cold fluid barrier may include a cold vapor barrier by one example. In another example, the cold fluid barrier includes a molten metal barrier. In another example, the cold fluid barrier includes water or steam. In another approach, the cold fluid barrier includes air or hydrogen. In yet another example, the cold fluid barrier includes methane. The cold fluid barrier may also include other fluids as known in the art or a combination of fluids. By one approach, the cold fluid barrier includes a fluid that comprises at least a portion of the process stream.

Figure 13:
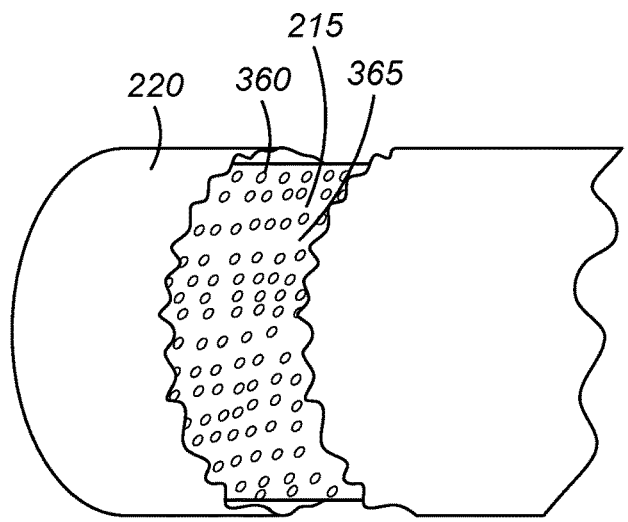
FIG. 13 is a perspective cut-away view showing portions of the supersonic reactor of FIG. 1 in accordance with various embodiments described herein.

The film barrier may be provided over the internal surface of the portion of the reactor shell 11 in various manners. Referring to FIG. 13, in one approach, the reactor shell 11 includes openings 360 through at least a portion thereof to allow cold fluid to pass therethrough and form a cold fluid barrier. This may take the form of slots that discharge into the core flow. In another approach, the reactor shell 11 may include a porous wall 365 that facilitates cold fluid leaking therethrough to provide the fluid barrier. By one approach, the reactor shell may include passageways (not shown) similar to those described above with regard to the active cooling system and a cold fluid for forming the cold fluid barrier may be provided therethrough. In this approach, manifold tubing may be provided to introduce the cold fluid through the passageways and openings. In another approach, the reactor shell 11 may include an inner shell 215 and an outer shell 220 as described previously, and the inner shell 215 may include openings or comprise a porous wall over at least a portion of the inner shell 215. In this approach, cold fluid may be passed through the channel or passageways defined between the outer shell 220 and the inner shell 215 so that leaks through the porous wall inner shell 215 to form the cold fluid barrier over an inner surface of the portion of the inner shell 215. Likewise, where a liner 260 is provided inside of the reactor shell 11, as described above with regard to FIG. 6, the liner may be a porous or penetratable liner to allow cold fluid to pass through the liner and form a cold fluid barrier on an inner surface thereof. The film barrier may also be formed along the inner surface of the portion of the reactor shell 11 by other methods, including those known in the art.

In another approach, the wall may contain a plethora of small holes 360 that discharge the fluid in a film, forming a full coverage film cooled surface.

In another approach, the wall may contain slots or louvers which are supplied with coolant and form a cooling film by discharging the coolant along the wall in a downstream direction. The film barrier 350 may also be formed along the inner surface of the portion of the reactor shell 11 by other methods, including those known in the art.

In another approach, the impingement method maybe combined with the full coverage film cooling method, wherein the impingement fluid after impacting the hot wall is discharged through the film cooling holes 360 in such wall 365 providing two cooling effects.

In this manner, by providing a film barrier 350 over an inner surface of at least a portion of the reactor shell 11, deterioration of the reactor shell 11 may be restricted during operation of the supersonic reactor 5. The film barrier may reduce the temperature that the reactor shell 11 is exposed to during operation by providing a barrier to the hot core fluid and convectively cooling the wall with the film at the film cooling temperature.

The cooling system may incorporate various mechanisms as described above to provide the optimum combination for highest operating efficiency.

The foregoing description provides several approaches with regard to a reactor shell 11 or a portion of a reactor shell 11. In this manner, it should be understood that at least a portion of the reactor shell 11 may refer to the entire reactor shell 11 or it may refer to less than the entire reactor shell as will now be described in further detail. As such, the preceding description for ways to improve the construction and/or operation of at least a portion of the reactor shell 11 may apply generally to any portion of the reactor shell and/or may apply to the following specifically described portions of the reactor shell.

It has been identified that certain portions or components of the reactor shell 11 may encounter particularly harsh operation conditions or specific problems that are peculiar to that portion or component. Thus, according to various approaches, certain aspects of the preceding description may apply only to those portions or components were a particular problem has been identified. Locations around fuel injector (s) 30 and feedstock injector(s) 45 are examples of locations that may benefit from local film barriers or film cooling or impingement or locally positioned convective cooling passages.

One zone of the supersonic reactor 5 that encounters particularly harsh operating conditions during operation thereof is the combustion zone 25. In the combustion zone 25 the fuel stream is combusted in the presence of oxygen to create the high temperature carrier stream. Temperatures in the combustion zone 25 may be the highest temperatures present in the reactor chamber 15, and may reach temperatures of between about 2000° and about 3500° C. in one example, and between about 2000° and about 3200° C. in another example. Thus a particular problem that has been identified in the combustion zone 25 is melting of the reactor shell 11 at the combustion zone 25 and oxidation of the combustor walls with the presence of oxygen. The portion of the reactor shell in a combustion zone 25 may be referred to as the combustion chamber 26.

Another zone of the supersonic reactor 5 that encounters particularly harsh operating conditions includes the supersonic expansion zone 60, and particularly the supersonic expander nozzle 50 located therein. Specifically, due to the high temperature carrier gas traveling at near supersonic or supersonic speeds through the expander nozzle 50, the expander nozzle 50 and/or other portions of the supersonic expansion zone 60 may be particularly susceptible to erosion.

Similarly, other portions of the supersonic reactor including a diffuser zone 60, a mixing zone 55, the reactor zone 65, and the quench zone may encounter harsh operating conditions during operation of the supersonic reactor 5. Additional equipment or components that are used in conjunction with the supersonic reactor 5 may also face similar problems and harsh operation conditions, including, but not limited to, nozzles, lines, mixers, and exchangers.

Due to unique problems and operating conditions to which individual portions or components of the supersonic reactor may be exposed, these individual portions or components may be formed, operated, or used in accordance with the various approaches described herein, while other portions or components are formed, operated, or used in accordance with other approaches, that may or may not be described herein.

Figure 11:
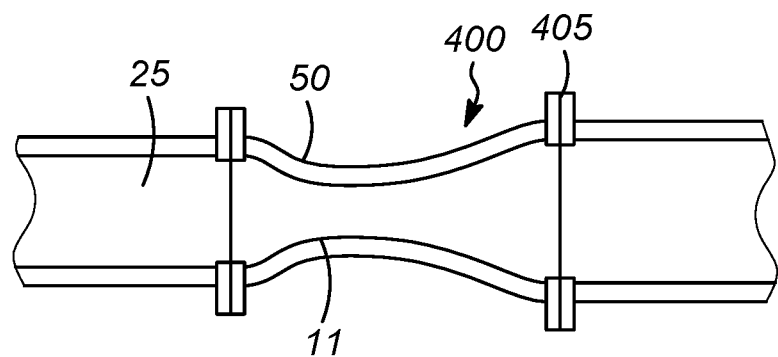
FIG. 11 is a partial side cross-sectional view showing portions of the supersonic reactor of FIG. 1 in accordance with various embodiments described herein.

Because different components or portions of the supersonic reactor 5 may be formed or operate differently, the supersonic reactor 5, including the reactor shell 11, may be made as separate parts and assembled to form the supersonic reactor 5 or the reactor shell 11. In this regard, the supersonic reactor 5 and/or the reactor shell 11 may include a modular configuration wherein individual modules or components 400 can be assembled together as shown in FIG. 11. By one approach at least some portions or components 400 of the assembled a supersonic reactor or reactor shell 11 may not be attached, instead the gases or fluids therein may be contained by differential pressure adjustment between components. In other approaches, the modules or components 400 may be connected together for example by flanges 405 sealed at cooled locations of the interface between the components. Similarly, different components, portions, or modules 400 may include different aspects provided in the description above. For example, some modules or components 400 may include active cooling, a film barrier, inner and outer layers, inner and outer shells, or other aspects described above, while other portions, modules, or components 400 may include different aspects.

According to one approach, one or more components or modules 400 may be removed and replaced during operation of the supersonic reactor 5 or during downtime thereof. For example, because the supersonic expansion nozzle 50 may deteriorate more quickly than other components of the reactor, the nozzle 50 may be removable so that it can be replaced with a new nozzle upon deterioration thereof. In one approach, the plurality of supersonic reactors 5 may be provided in parallel or in series with one or more supersonic reactors in operation and one or more supersonic reactors in standby so that if maintenance or replacement of one or more components of the operating supersonic reactor 5 is required, the process may be switched to the standby supersonic reactor to continue operation.

Further, the supersonic reactors may be oriented horizontally as illustrated in FIG. 1, or vertically (not shown). Where the reactor is configured vertically, the flow of the carrier and feed streams therethrough may be vertically up in one approach. The flow of the carrier and feed streams may be vertically down in another approach. In one approach the supersonic reactor may be oriented such that it is free draining to prevent the accumulation of liquid in the quench zone 72. In another approach the reactor may be oriented vertically (90° from horizontal) or horizontally (0° from horizontal) as indicated above or may be oriented at an angle between 0° and 90° with the reactor inlet at an elevation above the reactor outlet. In another embodiment the outlet 80 may include two or more outlets, including a primary outlet 80 for the main vapor phase flow and a secondary outlet 81 to drain liquid. In one approach liquid is injected to quench zone 72 and is not fully vaporized. This may occur during transient or steady state mode of operation. The secondary outlet may be operated continuously or intermittently as needed.

In one approach, the reactor shell 11 is sealed at one end and includes a plenum at an end opposite thereof.

By one approach, the reactor shell 11 may include a pressure relief device 218 as illustrated in FIG. 4. In one approach, the pressure relief device 218 includes a rupture disc. In another approach, the pressure relief device 218 includes a relief valve.

Figure 14:
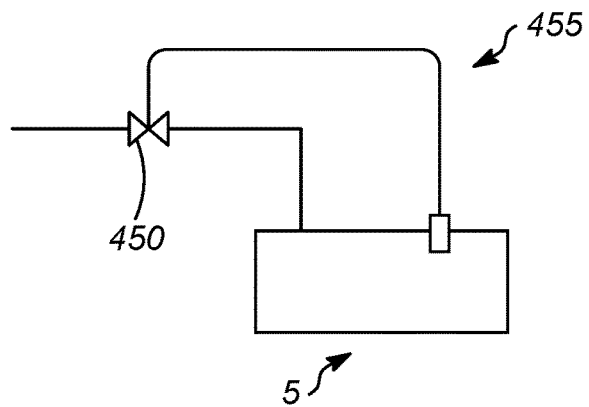
FIG. 14 is a schematic view of a supersonic reactor in accordance with various embodiments described herein.

In one approach, as shown in FIG. 14, the supersonic reactor 5 may include an isolation valve 450 at an inlet thereof. The supersonic reactor may also include a control system 455 to detect a change in pressure in the event of a blowout. The control system 455 may be configured to isolate the inlet in response thereto. In one approach, the inlet is a fuel stream 4 inlet.

According to one approach, the supersonic reactor 5 includes magnetic containment to contain reactants within the reaction chamber 15.

According to another approach, the supersonic reactor 5 may include hydrogen generation to generate hydrogen from the reactor effluent stream.

In one example, the reactor effluent stream after pyrolysis in the supersonic reactor 5 has a reduced methane content relative to the methane feed stream ranging from about 15 mol-% to about 95 mol-%. In another example, the concentration of methane ranges from about 40 mol-% to about 90 mol-% and from about 45 mol-% to about 85 mol-% in another example.

In one example the yield of acetylene produced from methane in the feed in the supersonic reactor is between about 40% and about 95%. In another example, the yield of acetylene produced from methane in the feed stream is between about 50% and about 90%. Advantageously, this provides a better yield than the estimated 40% yield achieved from previous, more traditional, pyrolysis approaches.

By one approach, the reactor effluent stream is reacted to form another hydrocarbon compound. In this regard, the reactor effluent portion of the hydrocarbon stream may be passed from the reactor outlet to a downstream hydrocarbon conversion process for further processing of the stream. While it should be understood that the reactor effluent stream may undergo several intermediate process steps, such as, for example, water removal, adsorption, and/or absorption to provide a concentrated acetylene stream, these intermediate steps will not be described in detail herein.

Referring to FIG. 2, the reactor effluent stream having a higher concentration of acetylene may be passed to a downstream hydrocarbon conversion zone 100 where the acetylene may be converted to form another hydrocarbon product. The hydrocarbon conversion zone 100 may include a hydrocarbon conversion reactor 105 for converting the acetylene to another hydrocarbon product. While FIG. 2 illustrates a process flow diagram for converting at least a portion of the acetylene in the effluent stream to ethylene through hydrogenation in hydrogenation reactor 110, it should be understood that the hydrocarbon conversion zone 100 may include a variety of other hydrocarbon conversion processes instead of or in addition to a hydrogenation reactor 110, or a combination of hydrocarbon conversion processes. Similarly, unit operations illustrated in FIG. 2 may be modified or removed and are shown for illustrative purposes and not intended to be limiting of the processes and systems described herein. Specifically, it has been identified that several other hydrocarbon conversion processes, other than those disclosed in previous approaches, may be positioned downstream of the supersonic reactor 5, including processes to convert the acetylene into other hydrocarbons, including, but not limited to: alkenes, alkanes, methane, acrolein, acrylic acid, acrylates, acrylamide, aldehydes, polyacetylides, benzene, toluene, styrene, aniline, cyclohexanone, caprolactam, propylene, butadiene, butyne diol, butandiol, C2-C4 hydrocarbon compounds, ethylene glycol, diesel fuel, diacids, diols, pyrrolidines, and pyrrolidones.

A contaminant removal zone 120 for removing one or more contaminants from the hydrocarbon or process stream may be located at various positions along the hydrocarbon or process stream depending on the impact of the particular contaminant on the product or process and the reason for the contaminants removal, as described further below. For example, particular contaminants have been identified to interfere with the operation of the supersonic flow reactor 5 and/or to foul components in the supersonic flow reactor 5. Thus, according to one approach, a contaminant removal zone is positioned upstream of the supersonic flow reactor in order to remove these contaminants from the methane feed stream prior to introducing the stream into the supersonic reactor. Other contaminants have been identified to interfere with a downstream processing step or hydrocarbon conversion process, in which case the contaminant removal zone may be positioned upstream of the supersonic reactor or between the supersonic reactor and the particular downstream processing step at issue. Still other contaminants have been identified that should be removed to meet particular product specifications. Where it is desired to remove multiple contaminants from the hydrocarbon or process stream, various contaminant removal zones may be positioned at different locations along the hydrocarbon or process stream. In still other approaches, a contaminant removal zone may overlap or be integrated with another process within the system, in which case the contaminant may be removed during another portion of the process, including, but not limited to the supersonic reactor 5 or the downstream hydrocarbon conversion zone 100. This may be accomplished with or without modification to these particular zones, reactors or processes. While the contaminant removal zone 120 illustrated in FIG. 2 is shown positioned downstream of the hydrocarbon conversion reactor 105, it should be understood that the contaminant removal zone 120 in accordance herewith may be positioned upstream of the supersonic flow reactor 5, between the supersonic flow reactor 5 and the hydrocarbon conversion zone 100, or downstream of the hydrocarbon conversion zone 100 as illustrated in FIG. 2 or along other streams within the process stream, such as, for example, a carrier fluid stream, a fuel stream, an oxygen source stream, or any streams used in the systems and the processes described herein.

One embodiment of the present disclosure is directed to apparatus and methods for converting methane in a hydrocarbon stream to acetylene using a supersonic flow reactor, while minimizing the possibility of explosion due to the formation of copper acetylides from a chemical reaction between the acetylene gas generated and the copper of the inner layer. The methane pyrolysis reactor zone presents a strong reducing environment in the presence of hydrogen and high temperature. Cu or CuO is found to interact readily with acetylene leading to copper acetylide formation.

A coating may be applied to an inner surface of the inner layer to provide a barrier between the acetylene gas generated and the copper of the inner layer in order to prevent the formation of acetylides. Thus the inner layer 210 may include a coating that is formed on an inner surface of the inner layer to form a barrier between the copper of the inner layer and the acetylene gas being generated. The coating can be a thin coating applied to the inner surface of the inner layer of the reactor shell and can be a material that does not react with acetylene. In one embodiment, examples of suitable coatings include those comprising nickel metal or an alloy of nickel or a mixture thereof. Specific examples alloys of nickel include NiCrAlY, NiCoCrAlY, CoNiCrAlY, and Ni—P. With a copper containing substrate, the nickel forms a solid solution which with thermal treatment forms a very strong bond resistant to thermal shock stress. It is further envisioned that the nickel or alloy of nickel coating may be in addition to a thermal barrier coating such as described above in order to slow down heat transfer. Other suitable coatings may be comprised of chromium, an alloy containing chromium, platinum, an alloy containing platinum, palladium, an alloy containing palladium, or mixtures thereof, or mixtures of any of the above with nickel or an alloy containing nickel.

The metal or alloy or mixture may be applied to surfaces of the reactor shell such as the inner surface of the inner layer by a variety of known metallization processes. Suitable examples include electroplating using electrical current, electroless plating which does not use electrical current, or by applying using plasma spray techniques. For example, pure nickel may be applied using an electroplating technique. This coating may not require post application thermal treatment, but adhesion can be improved with thermal exposure from about 482° C. to about 538° C. for about 1 to about 3 hours. The coating is dense and prevents copper contact with acetylene gas. Furthermore, the coating may be applied in combination with, for example, a stabilized zirconia coating as described earlier, in which case the dense coating provides not only a barrier to the formation of acetylide but is a heat transfer barrier as well. In another example, the coating of an alloy of nickel, such as NiCrAlY, may be applied using plasma spray technologies. This coating may not require post application thermal treatment but adhesion may be improved with thermal exposure from about 482° C. to about 538° C. for about 1 to about 3 hours. The coating is dense and prevents copper contact with acetylene gas. Furthermore, the coating may be applied in combination with, for example, a stabilized zirconia coating as described earlier, in which case the dense coating provides not only a barrier to the formation of acetylide but is a heat transfer barrier as well. In yet another embodiment, a Ni—P coating may be applied using electroless plating. As above, the coating may not require post application thermal treatment but adhesion may be improved with thermal exposure from about 482° C. to about 538° C. for about 1 to about 3 hours. The coating is dense and prevents copper contact with acetylene gas. Furthermore, the coating may be applied in combination with, for example, a stabilized zirconia coating as described earlier, in which case the dense coating provides not only a barrier to the formation of acetylide but is a heat transfer barrier as well.

While there have been illustrated and described particular embodiments and aspects, it will be appreciated that numerous changes and modifications will occur to those skilled in the art, and it is intended in the appended claims to cover all those changes and modifications which fall within the true spirit and scope of the present disclosure and appended claims.

The invention claimed is:

1. An apparatus for producing acetylene from a feed stream comprising methane comprising:
   a supersonic reactor for receiving the methane feed stream and heating the methane feed stream to a pyrolysis temperature;
   a reactor shell of the supersonic reactor for defining a reactor chamber;

a combustion zone of the supersonic reactor for combusting a fuel source to provide a high temperature carrier gas passing through the reactor space at supersonic speeds to heat and accelerate the methane feed stream to a pyrolysis temperature;

an outer layer of the reactor shell for providing structural support thereto;

an inner layer of the reactor shell having a thermal conductivity of between about 200 and about 500 W/m-K for conducting heat from the reactor chamber the inner layer comprising at least copper chrome, copper chrome zinc, copper chrome niobium, copper nickel and copper nickel tungsten and mixtures thereof; and a coating comprising nickel metal, an alloy of nickel, chromium metal, an alloy of chromium, platinum metal, an alloy of platinum, palladium, or an alloy of palladium, or mixtures thereof applied to an inner surface of the inner layer of the reactor shell.

2. The apparatus of claim 1 wherein the coating comprises NiCrAlY, or NiCoCrAlY, or CoNiCrAlY, or Ni—P, or mixtures thereof.

3. The apparatus of claim 1 wherein the coating comprises NiCrAlY.

4. The apparatus of claim 1 wherein the coating is electroplated onto the inner surface of the inner layer.

5. The apparatus of claim 4 wherein the coating is thermally treated at a temperature of from about 482° C. to about 538° C. for about 1 to about 3 hours.

6. The apparatus of claim 4 wherein the coating comprises nickel metal.

7. The apparatus of claim 1 wherein the coating is applied to the inner surface of the inner layer using plasma spray techniques.

8. The apparatus of claim 7 wherein the coating is thermally treated at a temperature of from about 482° C. to about 538° C. for about 1 to about 3 hours.

9. The apparatus of claim 7 wherein the coating comprises NiCrAlY.

10. The apparatus of claim 1 wherein the coating is applied to the inner surface of the inner layer using an electroless plating process.

11. The apparatus of claim 10 wherein the coating is thermally treated at a temperature of from about 482° C. to about 538° C. for about 1 to about 3 hours.

12. The apparatus of claim 10 wherein the coating comprises Ni—P.

13. The apparatus of claim 1 wherein the coating further comprises a material capable of providing a thermal barrier.

14. The apparatus of claim 1 wherein the coating further comprises yttria-stabilized zirconia, lanthanum hexaluminate, rare earth-doped lanthanum hexaluminate, hafnium carbide, tungsten, or mixtures thereof.

15. The apparatus of claim 1 wherein the reactor shell is a composite having the inner and outer layers.

16. The apparatus of claim 1 wherein the inner layer and outer layers comprise separate castings and the castings are brazed together.

17. The apparatus of claim 1 further comprising one or more intermediate layers between the outer layer and the inner layer.

18. The apparatus of claim 1 further comprising one or more layers positioned outside of the outer layer.

19. A process for producing acetylene from a feed stream comprising methane comprising:

introducing the feed stream to a supersonic reactor wherein the supersonic reactor comprises:

a reactor shell of the supersonic reactor for defining a reactor chamber;

a combustion zone of the supersonic reactor for combusting a fuel source to provide a high temperature carrier gas passing through the reactor space at supersonic speeds to heat and accelerate the methane feed stream to a pyrolysis temperature;

an outer layer of the reactor shell for providing structural support thereto;

an inner layer of the reactor shell having a thermal conductivity of between about 200 and about 500 W/m-K for conducting heat from the reactor chamber the inner layer comprising at least copper chrome, copper chrome zinc, copper chrome niobium, copper nickel and copper nickel tungsten and mixtures thereof; and a coating comprising a coating comprising nickel metal, an alloy of nickel, chromium metal, an alloy of chromium, platinum metal, an alloy of platinum, palladium, or an alloy of palladium, or mixtures thereof applied to an inner surface of the inner layer of the reactor shell;

combusting a fuel source to provide a high temperature carrier gas passing through the reactor at supersonic speeds to heat and accelerate the methane feed stream to a pyrolysis temperature, wherein upon heating and accelerating the methane stream, acetylene is generated; and preventing formation of acetylides in the reactor by employing the coating that prevents the acetylene from contacting the copper of the inner layer of the reactor.

* * * * *